(12) United States Patent
Koyama et al.

(10) Patent No.: US 8,492,142 B2
(45) Date of Patent: Jul. 23, 2013

(54) FREEZE-DRIED PRODUCT FOR INTRODUCING NUCLEIC ACID, OLIGONUCLEIC ACID OR DERIVATIVE THEREOF

(75) Inventors: Yoshiyuki Koyama, Tokyo (JP); Tomoko Ito, Chiba (JP)

(73) Assignee: Yoshiyuki Koyama, Tokyo (JP)

( * ) Notice: Subject to any disclaimer, the term of this patent is extended or adjusted under 35 U.S.C. 154(b) by 0 days.

(21) Appl. No.: 13/396,875

(22) Filed: Feb. 15, 2012

(65) Prior Publication Data

US 2012/0202283 A1 Aug. 9, 2012

Related U.S. Application Data

(62) Division of application No. 12/227,394, filed as application No. PCT/JP2007/060002 on May 16, 2007, now abandoned.

(30) Foreign Application Priority Data

May 17, 2006 (JP) .................................. 2006-138201

(51) Int. Cl.
*C12N 15/00* (2006.01)
(52) U.S. Cl.
USPC ....................................... 435/320.1; 977/704
(58) Field of Classification Search
None
See application file for complete search history.

(56) References Cited

U.S. PATENT DOCUMENTS

| 6,689,600 | B1 * | 2/2004 | Wu et al. | ..................... 435/235.1 |
| 7,235,391 | B2 * | 6/2007 | Wu et al. | ..................... 435/235.1 |
| 2005/0002998 | A1 * | 1/2005 | Chang et al. | ................... 424/450 |

FOREIGN PATENT DOCUMENTS

| EP | 1 439 199 A1 | 7/2004 |
| JP | 2005-176830 A | 7/2005 |

OTHER PUBLICATIONS

Ito, Tomoko et al, "Hyaluronic Acid as a Self-Assembled Coating of Plasmid/Polycation Complexes for Cell-Specific Gene Delivery", Polymer Preprints, Japan, 53$^{rd}$ SPSJ Symposium on Macromolecules, Sep. 1, 2004, pp. 3018-3019, vol. 53, No. 2, Japan.
Ito, Tomoko et al, "Hyaluronic acid and its derivative as a multifunctional gene expression enhancer: Protection from non-specific interactions, adhesion to targeted cells, and transcriptional activatilon", Journal of Controlled Release, Mar. 27, 2006, pp. 382-388, vol. 112, No. 3.
Peer, Dan et al, "Hyaluronan is a key component in cryoprotection and formulation of targeted unilamellar liposomes", Biochimica et Biophysica Acta, 2003, pp. 76-82, vol. 1612, No. 1.
Kowk Kai Y. et al, "Strategies for maintaining the particle size of peptide DNA condensates following freeze-drying", International Journal of Pharmaceutics, 2000, pp. 81-88. vol. 203, No. 1-2.
Allison S. Dean et al, "Stabilization of lipid/DNA complexes during the freezing step of the lyophilization process: the particle isolation hypothesis", Biochimica et Biophysica Acta, 2000, pp. 127-138, vol. 1468.
Ruponen, Marika et al, "Extracellular and intracellular barriers in non-viral gene delivery", Journal of Controlled Release, 2003, pp. 213-217, vol. 93, No. 2.
Torchilin. V.P. et al, "p-Nitrophenylcarbonyl-PEG-PE-liposomes: fast and simple attachment of specific ligands, including monoclonal antibodies, to distal ends of PEG chains via p-nitrophenylcarbonyl groups", Biochimica et Biophysica Acta, 2001, pp. 397-411, vol. 1511.
Koyama, Yoshiyuki et al., "Novel poly(ethylene glycol) derivatives with carboxylic acid pendant groups: synthesis and their protection and enhancing effect of non-viral gene transfection systems", J. Biomater. Sci. Polymer Edn, 2003, pp. 515-531, vol. 14, No. 6.
Molina, Marion d.C. et al, "Maintenance of Nonviral Vector Particle Size during the Freezing Step of the Lyophilization at Low Osmolalities: Concentrating Suspensions by Rehydration to Reduced Volumes", Journal of Pharmaceutical Sciences, Jun. 2005, pp. 1226-1236, vol. 94, No. 6.
Written Opinion of the International Searching Authority PCT/ISA/237 in International application PCT/JP2007/060002 and Notification of Transmittal PCT/ISA/338 mailed Dec. 24, 2008.
International Search Report in International application PCT/JP2007/060002, Mailed: Jul. 7, 2007.
Cherng et al., (1997), "Freeze-Drying of Poly(2-dimethylamino) ethyl (Metacrylate-Based Gene Delivery System," *Pharmaceutical Research*, 14(2): 1838-41.
Ji et al., (2005), "Construction of Polycation-Based Non-Viral DNA Nanoparticles and Polyanion Multilayers via Layer-by-Layer Self-Assembly," *Macromolecular Rapid Communications*, 26: 1633-38.
Berton M et al, "Highly loaded nanoparticulate carrier using an hydrophobic antisense oligonucleotide complex", European Journal of Pharmaceutical Sciences, Dec. 1999, pp. 163-170, vol. 9, No. 2, Elsevier Science B.V.
Vinogradov S V et al, "Self-assembly of polyamine-poly(ethylene glycol) copolymers with phosphorothioate oligonucleotides", Bioconjugate Chemistry, Nov. 1, 1998, pp. 805-812, vol. 9, No. 6, ACS, Washington, D.C., U.S.A.
Cortesi R et al, "Effect of DNA complexation and freeze-drying on the physicochemical characteristics of cationic liposomes", Antisense and Nucleic Acid Drug Development, Jun. 3, 2000, pp. 205-215, vol. 10, No. 3.
Supplementary European Search Report (3 pages) in corresponding EP application 07743437.1 (Feb. 4, 2010).
Anchordoquy, Thomas J. et al, "Low Molecular Weight Dextrans Stabilize Nonviral Vectors During Lyophilization at Low Osmolaties: Concentrating Suspensions by Rehydration to Reduced Volumes", Journal of Pharmaceutical Sciences, Jun. 2005, pp. 1226-1236, vol. 94, No. 6.

(Continued)

*Primary Examiner* — Robert M Kelly
(74) *Attorney, Agent, or Firm* — Holtz Holtz Goodman & Chick PC

(57) ABSTRACT

A freeze-dried product of a complex containing (i) a nucleic acid, an oligonucleic acid or a derivative thereof, (ii) polyethyleneimine and (iii) hyaluronic acid or chondroitin sulfate. The freeze-dried product can be used to introduce a nucleic acid or an oligonucleotide into a cell.

4 Claims, 11 Drawing Sheets

OTHER PUBLICATIONS

Japanese Office Action dated Feb. 26, 2013, which issued in counterpart Japanese Patent Application No. 2008-515578, and an English-language translation thereof.

Taylor K.C. Armstrong et al., "Effects of PEGylation on the Preservation of Cationic Lipid/DNA Complexes during Freeze-Thawing and Lyophilization," *Journal of Pharmaceutical Sciences*, (2002), vol.12, pp. 2549 to 2558.

Herre Talsma et al., "Stabilization of gene delivery systems by freeze-drying," *International Journal of Pharmaceutics*, (1997), vol. 157, pp. 233 to 238.

Thomas J. Anchorodoquy et al., "Maintenance of Transfection Rates and Physical Characterization of Lipid/Dna Complexes after Freeze-Drying and Rehydration," *Archives of Biochemistry and Biophysics*, (1997), vol. 348, No 1, pp. 199 to 206.

\* cited by examiner

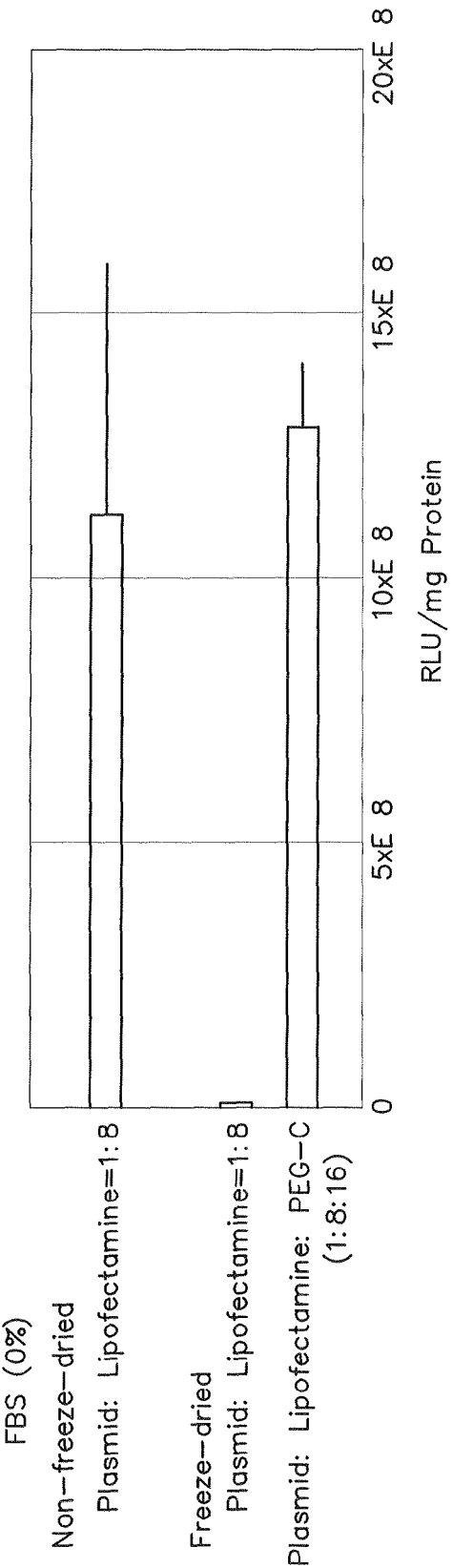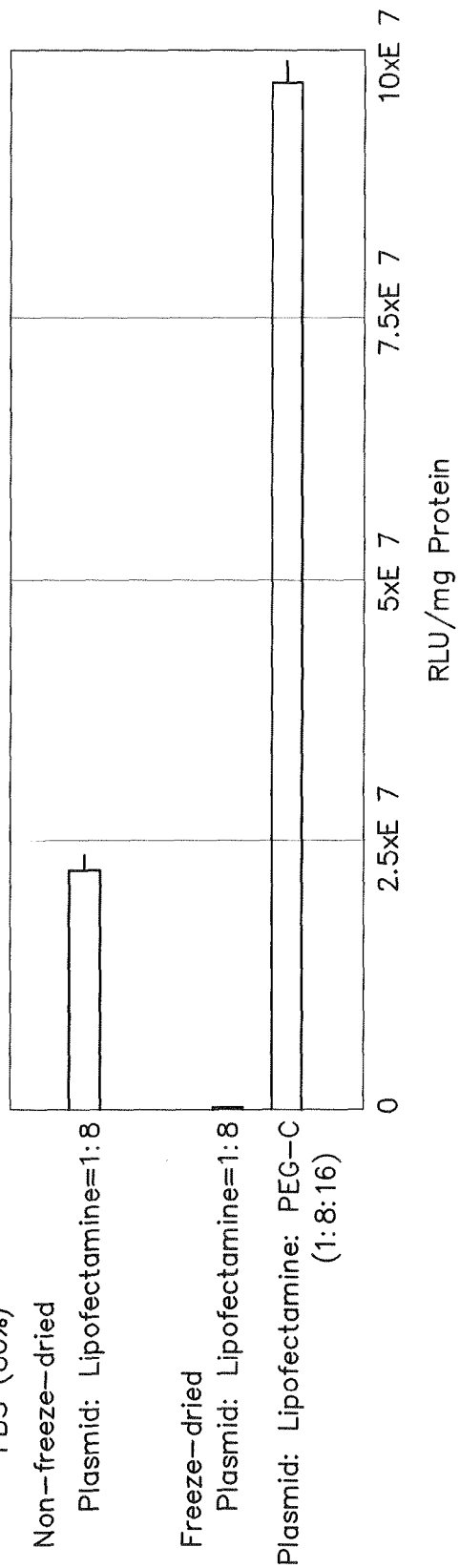
FIG. 5A
FIG. 5B

FREEZE-DRIED PRODUCT FOR INTRODUCING NUCLEIC ACID, OLIGONUCLEIC ACID OR DERIVATIVE THEREOF

CROSS-REFERENCE TO RELATED APPLICATIONS

This application is a divisional application of application Serial No. 22/227,394 filed Nov. 14, 2008 (abandoned), which is the United States national phases application under 35 USC 371 of International application PCT/JP2007/060002 filed May 16, 2007. The entire contents of each of application Ser. No. 12/227,394 and International application PCT/JP2007/06002 are hereby incorporated by reference herein.

TECHNICAL FIELD

The present invention relates to a freeze-dried product of a complex containing a nucleic acid, oligonucleic acid or derivative thereof; a cationic polymer, or cationic lipid or aggregate containing the same; and, an anionic polymer, for the purpose of introducing a nucleic acid, oligonucleic acid or derivative thereof into cells, a preparation method of the same, and a preparation, reagent and kit for introducing a nucleic acid, oligonucleic acid or derivative thereof containing the same.

BACKGROUND ART

Gene therapy and antisense treatment methods are currently used practically for treating congenital genetic diseases, cancer cells or AIDS by introducing an intended gene, antisense oligonucleic acid or derivative thereof into cells and expressing that gene or function, and studies are being conducted on various types of vectors for use as carriers for introducing genes (DNA), antisense oligonucleic acids and derivatives thereof into cells.

Research is being conducted on cationic substances such as cationic polymers, cationic liposomes and cationic lipids for use as one such type of vector in the form of a non-viral vector that eliminates concerns over safety, has favorable efficiency, is free of immunogenicity and is easily prepared.

In methods using these cationic substances, since complexes of DNA and cationic substances are positively charged, aggregation ends up occurring due to interaction with blood cells and blood components such as albumin, thereby impairing the delivery to the target cells. Studies have been conducted on various methods to solve this problem, including coating a complex of nucleic acid and cationic polymer with a hyaluronic acid derivative (Patent Document 1: Japanese Unexamined Patent Publication No. 2005-176830); coating with polyethylene glycol (PEG) having a carboxyl group-containing side chain and sugar residue-containing side chain (Patent Document 2: Japanese Unexamined Patent Publication No. 2003-231748); and preventing complex aggregation by using PEG having a free carboxylic acid pendant group (Non-Patent Document 1: J. Biomater. Sci. Polymer Edn., Vol. 14, No. 6, pp. 515-531 (2003)).

Complexes of DNA and cationic substances modified in this manner exhibit low aggregation and exhibit favorable gene expression in cells. However, since these complexes are heterogeneous suspensions, they have poor storage performance, are required to be used promptly following preparation, and end up aggregating when prepared at high concentrations, thereby having the disadvantages of difficulty in adjusting concentration and bothersome handling. In addition, it was difficult to prepare these complexes with satisfactory reproducibility.

On the other hand, in the case of using the modified complex of DNA and cationic substance as described above to introduce a gene and the like, it is also important to control the size (particle diameter) of the complex. This is because, in the case of administering into blood or tissue, subsequent diffusion of the complex and the efficiency at which it is delivered and incorporated by cells greatly affect its pharmacological efficacy. In general, however, in the case of mixing ionic polymers such as cationic polymers to form a complex, the polymer ends up aggregating resulting in an increased likelihood of the formation of extremely large particles or fibrous complexes. In order to prevent this, it is necessary to make the concentrations of the solutions mixed extremely dilute. However, since preparations used for gene introduction and the like are required to have a certain minimal concentration, there was the problem of being unable to avoid the formation of large mass of aggregates. In addition, although methods are also considered consisting of first forming small complexes by mixing dilute solutions followed by concentrating, suitable means for concentration was unable to be achieved since the complex particles ended up rapidly aggregating.

Therefore, in order to solve these problems, studies were conducted on freeze-drying methods typically used to facilitate transport of biological preparations and enhance storage stability. However, since freeze-drying complexes of nucleic acids, oligonucleic acids or derivatives thereof with polycationic substances ends up impairment of the structure of the complex due to the freeze-drying, when used for gene introduction or introduction of oligonucleic acids, the complexes were confirmed to hardly demonstrate any functions as genes or antisense oligonucleic acids (Non-Patent Document 2: J. Pharm. Sci., Vol. 90, pp. 1445-1455 (2001)).

A method to solve these problems was proposed in which freeze-drying is carried out after adding a high concentration of monosaccharide or disaccharide (Non-Patent Document 3: Biochim. Biophys. Acta., 2000 Sep. 29, 1468 (1-2): 127-138). However, the amount of sugar required is 500 to 1000 times the amount of DNA in terms of the weight ratio, making this method impractical in consideration of the solution following rehydration having a much higher osmotic pressure than physiological conditions. In addition, monosaccharides and disaccharides do not offer advantageous effects for gene expression. In addition, the use of a neutral polysaccharide, dextran has been attempted to reduce osmotic pressure after rehydration (Non-Patent Document 4: J. Pharm. Sci., Vol. 94, pp. 1226-1236 (2005)). However, high molecular weight dextran greatly inhibits gene expression, and in the case of using low molecular weight dextran (molecular weight of about 3000), it was necessary to add dextran at a considerably high concentration of 100 times or more that of DNA in terms of the weigh ratio in order to prevent aggregation caused by freeze-drying (Non-Patent Document 4: J. Pharm. Sci., Vol. 94, pp. 1226-1236 (2005)). For use of this type of freeze-dried product in vivo, the freeze-dried product is required to be rehydrated with a small amount of water or solvent after freeze-drying to obtain the required concentration of DNA and then concentrated to a high concentration. As a result, the concentration of dextran following rehydration exceeds 10%, and there are limitations during the freeze-drying procedure such as on DNA concentration and cooling temperature, thereby making practical application difficult.

Patent Document 1: Japanese Unexamined Patent Publication No. 2005-176830
Patent Document 2: Japanese Unexamined Patent Publication No. 2003-231748
Non-Patent Document 1: J. Biomater. Sci. Polymer Edn., Vol. 14, No. 6, pp. 515-531 (2003)
Non-Patent Document 2: J. Pharm. Sci., Vol. 90, pp. 1445-1.455 (2001)
Non-Patent Document 3: Biochim. Biophys. Acta., 2000 Sep. 29, 1468 (1-2): 127-138
Non-Patent Document 4: J. Pharm. Sci., Vol. 94, pp. 1226-1236 (2005)

DISCLOSURE OF THE INVENTION

Problems to be Solved by the Invention

The inventors of the present invention conducted extensive studies to overcome the aforementioned problems, and as a result they found that if a freeze-dried product of a complex containing a nucleic acid, oligonucleic acid or derivative thereof; a cationic polymer, or cationic lipid or aggregate containing the same; and, an anionic polymer is introduced into cells, the introduced gene, oligonucleic acid or derivative thereof satisfactorily expresses the function thereof, thereby leading to completion of the present invention.

Means for Solving the Problems

The present invention relates to a freeze-dried product of a complex containing a nucleic acid, oligonucleic acid or derivative thereof; a cationic polymer, or cationic lipid or aggregate containing the same; and, an anionic polymer. In addition, the present invention relates to a preparation, reagent and kit containing the freeze-dried product for introducing a nucleic acid, oligonucleic acid or derivative thereof. Moreover, the present invention relates to a method for preparing the freeze-dried product comprising a step of forming a complex by mixing a nucleic acid, oligonucleic acid or derivative thereof; a cationic polymer, or cationic lipid or aggregate containing the same; and an anionic polymer, followed by a step of freeze-drying the complex. The present invention also relates to a method for introducing a gene, oligonucleic acid or derivative thereof into cells, the method using the freeze-dried product.

Effects of the Invention

The freeze-dried product of the present invention enables concentration to be adjusted easily, offers easy handling and has superior storage performance. In addition, since the freeze-dried product of the present invention contains an anionic polymer, a stable dispersion containing a complex of an extremely small size can be obtained at an arbitrary concentration even when rehydrating with a solvent to form a suspension or dilution at the time of use. Moreover, a nucleic acid, oligonucleic acid or derivative thereof can be efficiently introduced into cells without causing aggregation even during gene introduction, and satisfactory ability to express a function thereof is demonstrated by various types of administration methods such as local administration or intravenous administration.

BRIEF DESCRIPTION OF THE DRAWINGS

FIGS. 5A and 5B are graphs showing the results for Example

BEST MEANS FOR CARRYING OUT THE INVENTION

Figure 1:
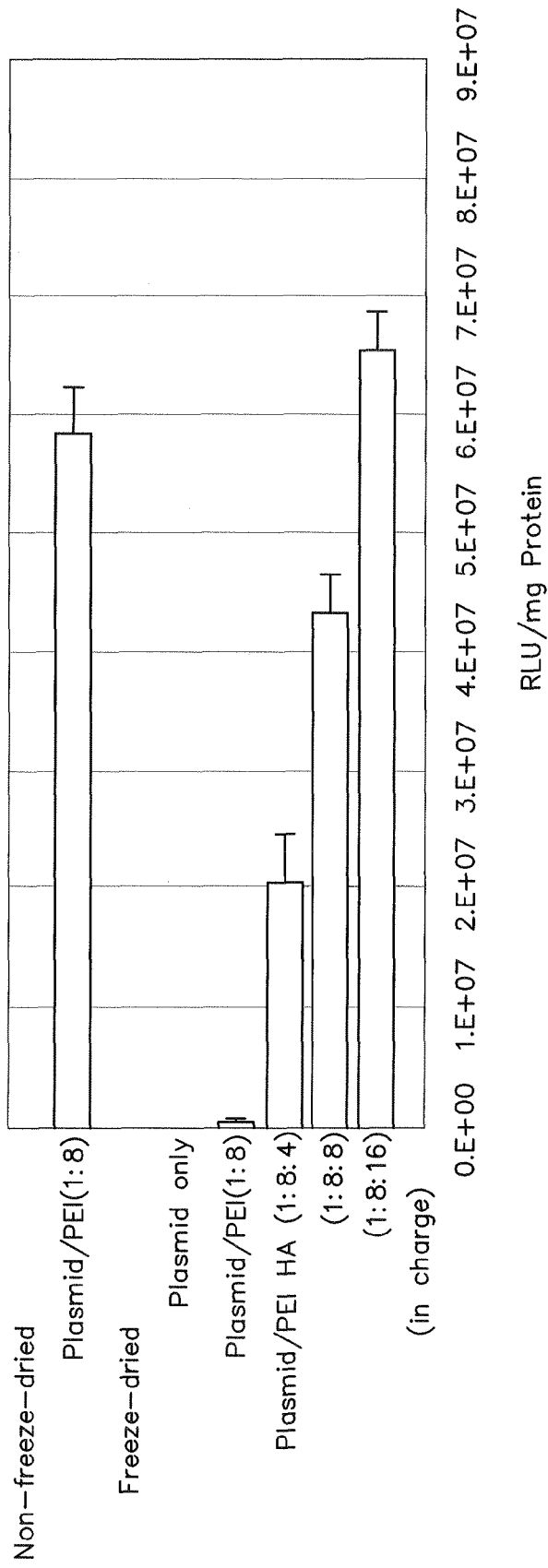
FIG. 1 is a graph showing the results for Example 1.

The freeze-dried product of the present invention is a freeze-dried product of a complex containing a nucleic acid, an oligonucleic acid or a derivative thereof; a cationic polymer, or cationic lipid or aggregate containing the same; and an anionic polymer. A nucleic acid, oligonucleic acid or derivative thereof in the complex forms a complex by ionic bonding wizh a cationic polymer, or cationic lipid or aggregate containing the same, and the cationic polymer or cationic lipid are further ionicly bonded with an anionic polymer. These components form a complex that is mainly coated with anionic polymer depending on the mixing ratio, mixing sequence and the like.

Any nucleic acid or oligonucleic acid and the like introduced for the purpose of gene therapy or antisense therapy can be used for the nucleic acid, oligonucleic acid or derivative thereof able to be used in the freeze-dried product of the present invention, specific examples of which include various types of nucleic acids, oligonucleic acids and derivatives thereof, such as various DNA and RNA (single-strand or double-strand) (such as plasmid DNA, double-stranded oligo RNA, mRNA, tRNA, rRNA or cDNA), sense or antisense oligonucleotides (including recombinants) and derivatives thereof, or ribozymes or mixtures thereof. In addition, the base portion or sugar portion of these nucleic acids may be modified or substituted as necessary. For example, plasmid DNA can be used preferably in the case of a nucleic acid, and oligo DNA or a derivative thereof in the form of S-oligo, double-stranded RNA for RNA interference or ribozyme RNA can be used preferably in the case of an antisense nucleic acid. Among them, plasmid DNA can be used particularly preferably.

Positively charged, naturally-occurring or synthetic polymers having a molecular weight of about 1,000 to 3,000,000 and having a plurality of, preferably five or more, functional groups capable of forming a complex with DNA in water can be used for the cationic polymer able to be used in the freeze-dried product of the present invention, and examples of such functional groups include organic amino groups such as optionally substituted amino groups, ammonium groups or salts thereof (and these groups may be mono- or poly-substituted with, for example, alkyl groups having 1 to 6 carbon atoms, phenyl groups and the like), imino groups, imidazolyl groups or guanidino groups. Examples of such cationic polymers include positively charged proteins and polypeptides; positively charged dendrimers; positively charged synthetic polymers; and positively charged polysaccharide derivatives or salts thereof and combinations thereof.

The molecular weight of positively charged proteins or positively charged polypeptides able to be used as cationic polymers in the freeze-dried product of the present invention is preferably about 1,000 to 500,000. Specific examples of such proteins and polypeptides include proteins or polypeptides such as protamine, histone, HelΔ1 or gelatin. In addition, examples also include polyamino acids containing positively charged amino acid residues. Specific examples of such polyamino acids containing positively charged amino acid residues include poly-L-lysine, polyarginine and polyornithine. Examples of salts of these proteins and polypeptides include hydrochlorides, sulfates, phosphates and borates.

Positively charged dendrimers having functional groups like those described above able to be used as cationic polymers refer to dendrimers having an optionally substituted amino group, ammonium group or salt thereof (and these groups may also be mono- or poly-substituted with, for example, alkyl groups having 1 to 6 carbon atoms, phenyl groups and the like) on the terminal or within a branched molecular chain, and the molecular weight thereof is preferably about 1,000 to 500,000. Specific examples of dendrimers include polyamide amine dendrimers and polylysine dendrimers. In addition, examples of dendrimer salts include hydrochlorides, sulfates, phosphates and borates.

Positively charged synthetic polymers able to be used as cationic polymers are synthetic polymers having a plurality of, preferably five or more, functional groups capable of forming a complex with DNA in water in a molecule thereof as previously described, and preferably having a molecular weight of 1,000 to 3,000,000. Specific examples of synthetic polymers include polyethyleneimines (including linear polyethyleneimines and branched polyethyleneimines), polymers or copolymers of 2-dimethylaminoethyl methacrylate, and polymers or copolymers of 2-trimethylaminoethyl methacrylate. The molecular weight of one example of synthetic polymers in the form of polyethyleneimines is preferably about 1,000 to 500,000, more preferably about 5,000 to 200,000 and most preferably about 10,000 to 100,000. In addition, examples of salts of polyethyleneimines include hydrochlorides, sulfates, phosphates and borates.

Positively charged polysaccharide derivatives able to be used as cationic polymers are polysaccharide derivatives having a plurality of, preferably five or more, functional groups capable of forming a complex with DNA in water in a molecule thereof, and having a molecular weight of preferably 1,000 to 3,000,000 and more preferably 5,000 to 500,000. Specific examples of such polysaccharides include chitosan and dextran derivatives introduced with functional groups as previously described. Among these, the molecular weight of chitosan is preferably about 1,000 to 500,000, more preferably about 5,000 to 200,000 and most preferably about 10,000 to 100,000. Examples of salts of chitosan include hydrochlorides and acetates. In addition, the molecular weight of dextran derivatives is preferably 3,000 to 1,000,000. Specific examples of such dextran derivatives include diethylaminoethyl dextran.

Even though the aforementioned cationic polymers are originally not positively charged, they can be used provided they become positively charged as a result of introducing a functional group such as an amino group, and may also be further modified with a sugar chain, oligopeptide or antibody and the like as necessary.

Examples of cationic lipids (including cationic cholesterol derivatives) able to be used in the freeze-dried product of the present invention include DC-Chol (3β-(N—(N',N-dimethylaminoethane) carbamoyl)cholesterol), DDAB (N,N-distearyl-N,N-dimethylammonium bromide), DMRI (N-(1,2-dimyristyloxyprop-3-yl)-N,N-dimethyl-N-hydroxyethyl ammonium bromide), DODAC (N,N-dioleyl-N,N-dimethylammonium chloride), DOGS (diheptadecylamidoglycyl-spermidine), DOSPA (N-(1-(2,3-dioleyloxy)propyl)-N-(2-(sperminecarboxamido)ethyl)-N,N-dimethylammonium trifluoroacetate), DOTAP (N-(1-(2,3-dioleyloxy)propyl)-N,N,N-trimethylammonium chloride) and DOTMA (N-(1-(2,3-dioleyloxy)propyl)-N,N,N-trimethylammonium chloride) or combinations thereof.

In addition, mixtures of the aforementioned cationic lipids (such as DOSPA) and neutral substances such as DOPE (dioleylphosphatidylethanolamine) or cholesterol can be used as aggregates containing cationic lipids. Preferable examples of aggregates containing cationic lipids include lipofectamine (liposome containing 3:1 w/w mixture of DOSPA and DOPE), lipofectin (liposome containing 1:1 w/w mixture of DOTMA and DOPE) and mixtures thereof.

In the freeze-dried product of the present invention, polyethyleneimines; protamine; HelΔ1; dendrimers such as polyamide amine dendrimers or polylysine dendrimers; chitosan; polymers or copolymers of 2-dimethylaminoethyl methacrylate or polymers or copolymers of 2-trimethylaminoethyl methacrylate can be used preferably as cationic polymer, while polyethyleneimines, polyamide amine dendrimers, polylysine dendrimers or chitosan can be used particularly preferably. In addition, lipofectamine (liposome containing a 3:1 w/w mixture of DOSPA and DOPE) can be used preferably, as a cationic lipid or aggregate containing the same.

Negatively charged, naturally-occurring or synthetic polymers containing an anionic group in a molecule thereof, having a molecular weight of about 500 to 4,000,000, and having a plurality of, preferably five or more, functional groups in a molecule thereof capable of forming a complex with a polycation in water can be used for the anionic polymer used in the freeze-dried product of the present invention, and examples of such functional groups include a carboxyl group, —OSO$_3$H group, —SO$_3$H group, phosphate group and salts thereof. Examples of such anionic polymers include amphoteric polymers.

Polysaccharides and derivatives thereof having functional groups selected from a carboxyl group, —OSO$_3$H group, —SO$_3$H group, phosphate group and salts thereof; polyamino acids containing an amino acid residue having negatively charged side chains; PEG derivatives having carboxyl side chains; synthetic polymers having functional groups selected from the group consisting of a carboxyl group, —OSO$_3$H group, —SO$_3$H group, phosphate group and salts thereof; polymers having functional groups selected from a carboxyl group, —OSO$_3$H group, —SO$_3$H group, phosphate group and salts thereof, as well as optionally substituted amino groups, ammonium groups or salts thereof (and these groups may be mono- or poly-substituted with, for example, alkyl groups having 1 to 6 carbon atoms, phenyl groups and the like); and combinations thereof can be used as an anionic polymer in the freeze-dried product of the present invention.

Glucosaminoglycans can be preferably used as a polysaccharide or derivative thereof having functional groups as described above able to be used as an anionic polymer in the freeze-dried product of the present invention. The molecular weight of such glucosaminoglycans is preferably 1,000 to 4,000,000 and more preferably 4,000 to 3,000,000. Specific examples of such glucosaminoglycans include hyaluronic acid, chondroitin, chondroitin sulfate, keratan sulfate, heparin and dermatan sulfate. Among them, hyaluronic acid can be used particularly preferably. Hyaluronic acid can also be used in the form of a salt or negatively charged derivative thereof. Although the molecular weight thereof may be 5,000 or more, it is preferably 10,000 or more and more preferably 100,000 to 3,000,000. Examples of salts of hyaluronic acid include sodium salts, potassium salts and ammonium salts. In addition, examples of derivatives of hyaluronic acid include those obtained by introducing polyethylene glycol, peptide, sugar, protein, hydroiodic acid, antibody or portions thereof into hyaluronic acid, and amphoteric derivatives having a positively charged portion by introducing spermine, spermidine, and the like are also included.

Polyamino acids containing an amino acid residue having a negatively charged side chain able to be used as an anionic polymer in the freeze-dried product of the present invention are polyamino acids preferably having a molecular weight of 500 to 1,000,000 and containing an amino acid residue having as a side chain thereof a carboxyl group, —O—$SO_3H$ group, —$SO_3H$ group, phosphate group or salt thereof. Specific examples of such polyamino acids include polyglutamic acid and polyaspartic acid.

PEG derivatives having a carboxyl side chain able to be used as an anionic polymer in the freeze-dried product of the present invention are PEG derivatives having a molecular weight of 500 or more, preferably 2,000 or more and more preferably 4,000 to 40,000 and having a plurality of, preferably five or more, carboxyl side chains per molecule of PEG. PEG derivatives having carboxyl side chains can also be used as salts thereof or negatively charged derivatives thereof. Examples of these salts include sodium salts, potassium salts and ammonium salts. Specific examples of such PEG derivatives include the PEG derivatives described in Non-Patent Document 1 (J. Biomater. Sci. Polymer Edn. Vol. 14, pp. 515-531 (2003)).

Synthetic polymers having functional groups selected from a carboxyl group, —O—$SO_3H$ group, —$SO_3H$ group, phosphate group and salts thereof able to be used as an anionic polymer in the freeze-dried product of the present invention are polymers or copolymers having a plurality of, preferably five or more, functional groups selected from a carboxyl group, —O—$SO_3H$ group, —$SO_3H$ group, phosphate group and salts thereof per molecule thereof, and preferably having a molecular weight of 500 to 4,000,000. Specific examples of such polymers or copolymers include polymers or copolymers of acrylic acid or methacrylic acid having a molecular weight of 1000 to 3,000,000, sulfuric acid esters of polyvinyl alcohol, and succinylated poly-L-lysine.

Polymers having functional groups selected from a carboxyl group, —$OSO_3H$ group, —$SO_3H$ group, phosphate group and salts thereof, as well as optionally substituted amino groups, ammonium groups or salts thereof (and these groups may be mono- or poly-substituted with alkyl groups having 1 to 6 carbon atoms, phenyl groups and the like), able to be used as an anionic polymer in the freeze-dried product of the present invention are polymers having a molecular weight of 500 or more, preferably 2,000 or more and more preferably 4,000 to 40,000 and having a plurality of, preferably five or more, functional groups selected from a carboxyl group, —$OS_3O$ group, —$SO_3H$ group, phosphate group and sales thereof per molecule thereof, as well as optionally substituted amino groups, ammonium groups or salts thereof as previously described. Preferable examples of such polymers include PEG derivatives having carboxyl group side chains and an equivalent amount or less of the aforementioned amino groups, ammonium groups or salts thereof, and specific examples include PEG derivatives able to be prepared using the method described in Non-Patent Document 5 (Macromol. Biosci., Vol. 2, pp. 251-256 (2002)).

Anionic polymers able to be used in the freeze-dried product of the present invention can be used even if they are usually not negatively charged provided they are made to be negatively charged by introducing functional groups such as a carboxyl group, and may be further modified with a sugar chain, oligopeptide or antibody and the like as necessary.

In the freeze-dried product of the present invention, hyaluronic acid, PEG derivatives having carboxyl side chains, anionic polymers such as polyacrylic acid or salts thereof can be preferably used as anionic polymers, while hyaluronic acid, PEG derivatives having carboxyl side chains or salts thereof can be used particularly preferably.

In addition, the use of an anionic polymer having the ability to specifically adhere to target cells for introducing a nucleic acid makes it possible to specifically introduce a nucleic acid into the target cells. For example, in the case of using hyaluronic acid for the anionic polymer, cells having cell surface molecules such as CD44, which specifically bond with hyaluronic acid, can be targeted. In addition, the use of an anionic polymer introduced with RGD peptide makes it possible to target numerous types of tumor cells, while the use of an anionic polymer introduced with a galactose side chain makes it possible to target liver cells or cells originating in the liver.

In the freeze-dried product of the present invention, preferable examples of combinations of a cationic polymer or cationic lipid or aggregate containing the same and an anionic polymer include polyethyleneimines and hyaluronic acid; polyethyleneimines and PEG derivatives having carboxyl side chains; aggregates containing DOSPA (such as lipofectamine (liposome containing 3:1 w/w mixture of DOSPA and DOPE)) and hyaluronic acid; and aggregates containing DOSPA (such as lipofectamine) and PEG derivatives having carboxyl side chains.

Although varying according to the types of target cells, nucleic acid, cationic polymer and the like, the molar ratio (negative charge:positive charge ratio) of each charged group of a nucleic acid, oligonucleic acid or derivative thereof and a cationic polymer, or cationic lipid or aggregate containing the same used in the freeze-dried product of the present invention may be 1:0.8 to 1:100, preferably 1:1 to 1:50 and more preferably 1:1.2 to 1:30. The blending ratio between a nucleic acid, oligonucleic acid or derivative thereof and a cationic polymer, or cationic lipid or aggregate containing the same refers to the molar ratio of each charged group, and more specifically indicates the molar ratio of negative charge attributable to phosphate anions of a nucleic acid, oligonucleic acid or derivative thereof to positive charge of a cationic polymer, or cationic lipid or aggregate containing the same, or functional groups able to be positively charged.

Although varying according to the types of target cells, nucleic acid, anionic polymer and the like, the molar ratio (negative charge:negative charge ratio) of each charged group between a nucleic acid, oligonucleic acid or derivative thereof to anionic polymer used in the freeze-dried product of the present invention may be 1:0.2 to 1:1000, preferably 1:0.2 to 1:100 and more preferably 1:1 to 1:60. The blending ratio between nucleic acid, oligonucleic acid or derivative thereof and anionic polymer refers to the molar ratio of each charged group, and more specifically indicates the molar ratio of negative charge attributable to phosphate anions of a nucleic acid, oligonucleic acid or derivative thereof to negative charge of the anionic polymer or functional groups able to be negatively charged.

For example, in the case of using hyaluronic acid for the anionic polymer, the blending ratio of nucleic acid to hyaluronic acid is 1:0.2 to 1:1000, preferably 1:0.2 to 1:100 and more preferably 1:1 to 1:60.

For example, in the case of using a PEG derivative having carboxyl side chains for the anionic polymer, the blending ratio of nucleic acid to PEG derivative having carboxyl side chains may be 1:0.2 to 1:1000, preferably 1:0.2 to 1:100 and more preferably 1:1 to 1:60.

In particular, in the case of using polyethyleneimine for the cationic polymer and hyaluronic acid for the anionic polymer, the blending ratio of nucleic acid to polyethyleneimine to hyaluronic acid is 1:2 to 60:1 to 240, preferably 1:4 to 24:1 to 160, more preferably 1:7 to 20:2 to 60 and particularly preferably 1:8 to 14:2 to 32.

In particular, in the case of using polyethyleneimine for the cationic polymer and a PEG derivative having carboxyl side chains for the anionic polymer, the blending ratio of nucleic acid to polyethyleneimine to PEG derivative having carboxyl side chains is 1:2 to 60:1 to 240, preferably 1:4 to 24:2 to 160, more preferably 1:7 to 20:2 to 60 and particularly preferably 1:8 to 14:4 to 32.

In particular, in the case of using lipofectamine (liposome containing 3:1 w/w mixture of DOSPA and DOPE) as an aggregate containing cationic lipid and hyaluronic acid for the anionic polymer, the blending ratio of nucleic acid to lipofectamine to hyaluronic acid is 1:1 to 50:0.2 to 240, preferably 1:1.2 to 48:0.2 to 160, more preferably 1:1.5 to 30:0.5 to 60, and particularly preferably 1:1.8 to 16:1 to 32.

In particular, in the case of using lipofectamine as an aggregate containing cationic lipid and a PEG derivative having carboxyl side chains for the anionic polymer, the blending ratio of nucleic acid to lipofectamine to PEG derivative having carboxyl side chains is 1:1 to 50:0.1 to 160, preferably 1:1.2 to 48:0.2 to 160, more preferably 1:1.5 to 30:0.5 to 60 and particularly preferably 1:1.8 to 16:2 to 32.

Although preferable blending ratios of nucleic acid, oligonucleic acid or a derivative thereof; cationic polymer or cationic lipid or aggregate containing the same; and anionic polymer contained in the freeze-dried product of the present invention are as described above, since optimum conditions fluctuate according to the number and type of cells introduced with nucleic acid and the like, the blending ratio can be suitably determined by a person with ordinary skill in the art according to the types of cells and nucleic acid used.

The freeze-dried product of the present invention can be prepared by a step of forming a complex by mixing the aforementioned nucleic acid, oligonucleic acid or derivative thereof, cationic polymer or cationic lipid or aggregate containing the same, and anionic polymer in the blending ratios described above, and a step of freeze-drying the complex. The order of mixing is preferably [1] nucleic acid, oligonucleic acid or derivative thereof, [2] cationic polymer or cationic lipid or aggregate containing the same, and [3] anionic polymer; or [1] nucleic acid, oligonucleic acid or derivative thereof, [2] anionic polymer, and [3] cationic polymer or cationic lipid or aggregate containing the same. The complex is formed as a result of the nucleic acid, oligonucleic acid or derivative thereof bonding with the cationic polymer or cationic lipid or aggregate containing the same by ionic bonding, followed by the cationic polymer or cationic lipid or aggregate containing the same bonding with the anionic polymer by ionic bonding. Alternatively, depending on the blending composition of each component, the outer shell of such a complex may be coated mainly with the anionic polymer resulting in the formation of a mode having a negative surface potential.

Next, the resulting complex is freeze-dried. Freeze-drying can be carried out under ordinary freeze-drying conditions such as under conditions consisting of drying under reduced pressure (preferably 5 to 100 mmHg and more preferably 10 mmHg) at an external temperature of −78 to 60° C. and preferably −30 to 40° C. The time required for drying varies according to the degree of depressurization and the amount of solvent, and is normally completed in 1 hour to 2 days.

The freeze-dried product of the present invention prepared in this manner can be used for various types of gene therapy, antisense therapy or introduction of a specific gene into humans and animals, and for the production of controlled, knockdown and knockout experimental animals and cells. More specifically, the freeze-dried product of the present invention can be used after converting to a rehydrate by suspending or dissolving in a solvent such as water, physiological saline, buffer, glucose solution or liquid medium prior to use. When rehydrating, the freeze-dried product is suspended or diluted using 100 to 10000 times (weight ratio) more of solvent than the nucleic acid, oligonucleic acid or derivative thereof, for example. Since a different amount or different type of solvent can be used from that prior to freeze-drying, comparatively high concentrations of suspensions or solutions (such as liquids containing 1 mg of DNA in 1 ml of liquid), which were difficult to prepare in the past, can be prepared easily.

Thus rehydrated freeze-dried product of the present invention can be used for introducing a nucleic acid and the like into cells by using any arbitrary method normally used to introduce a nucleic acid, oligonucleic acid or derivatives thereof into cells of the living body. Specific one includes an ex vivo method in which target cells placed in wells after having been removed from the body are treated with the rehydrated freeze-dried product of the present invention to introduce a gene or antisense nucleic acid and the cells are returned to the body to express the intended gene; or an in vivo and in situ method for directly introducing a gene or antisense nucleic acid, and so forth.

In addition, the freeze-dried product of the present invention can also be administered without rehydrating by means such as contacting with cells into which a nucleic acid and the like is to be introduced, subcutaneously transplanting into an animal in which a nucleic acid is to be introduced, or transplanting into, onto the surface of, or in the vicinity of a target tissue in which a nucleic acid is to be introduced.

Although varying according to the type of introduction method as described above or the disease, the amount of the freeze-dried product of the present invention applied to cells in terms of the amount of, for example, nucleic acid, oligonucleic acid or derivative thereof in an ex vivo method or in situ method is 0.2 to 10 μg/$10^4$ to $10^7$ cells per 1 to 2 cm diameter well, and in the case of an in vivo method, 5 to 100 μg/cm$^3$ of tumor, for example, in the case of local administration into a tumor, although varying considerably according to the administration site, and for example, 0.1 μg to 100 mg/organ in the case of administration into an organ such as the urinary bladder or 0.1 ng to 10 mg/kg of body weight in the case of systemic administration.

Any method employed in the field of gene therapy can be used as an in vivo method for directly administering into the body, examples of which include injecting a rehydrated freeze-dried product of the present invention intravenously, subcutaneously, intramuscularly, intraperitoneally, into a tumor or the vicinity of a tumor, inhaling through the nasal cavity, oral cavity or lungs, directly injecting into the urinary bladder or rectum, directly administering into tissue at the site of a lesion or a nearby blood vessel or implanting by supporting on a porous body or non-woven fabric and the like such as a gelatinous substance or sponge.

In addition, even when using a hydrate of the freeze-dried product of the present invention without rehydrating, the freeze-dried product in an amount as previously described can be used by an ex vivo method, in situ method or in vivo method as described above.

In the freeze-dried product of the present invention, together with the anionic polymer being neutralized., the neutralizing action of the positive charge of a complex of an ordinary nucleic acid, oligonucleic acid or derivative thereof and a cationic polymer or cationic lipid or aggregate containing the same is retained even after being administered into the living body or cells. As a result, interactions such as agglutination occurring between the complex and serum proteins, blood cells or the extracellular matrix and the like are inhibited. In addition, since enzymatic degradation of nucleic acids, oligonucleic acids or derivatives thereof is inhibited, nucleic acids are efficiently taken up by cells and expressed with high efficiency.

As has been described above, a hydrate of the freeze-dried product of the present invention can be used as a preparation or reagent for introducing a nucleic acid, oligonucleic acid or derivative thereof, or as a kit for introducing a nucleic acid, oligonucleic acid or derivative thereof.

The following provides a more detailed explanation of the present invention through Examples thereof.

Furthermore, these Examples are provided for the purpose of explaining the present invention, and do not limit the invention in any way.

Example 1

Gene Expression by Freeze-Dried Product of a Plasmid/Polyethyleneimine (PEI)/Hyaluronic Acid (HA) Complex A freeze-dried complex comprised of the three components of a gene, PEI and HA was incubated with mouse melanoma cell line derived B16 to confirm the expression of luciferase gene.

The same plasmid as that described in Non-Patent Document 6 (Biomacromolecules, Vol. 7, pp. 1274-1279) was used for the luciferase plasmid. Linear PEI (Polyscience, Inc.) having a molecular weight of Mw=25,000 was used for the PEI. Microbial hyaluronic acid (Nacalai-Tesque) was used for the HA. Phosphate Buffered Salts (tablet, Roman Industries) dissolved in ion exchange distilled water was used as PBS. This applies similarly to the following examples as well.
[Operation Procedure]
[1] 316 cells were seeded into a 24-well multiplate two days prior to gene introduction and then incubated for two nights using EMEM medium.
[2] 2 μl of an aqueous solution containing 1.3 g of luciferase plasmid was mixed with 2 μl of an aqueous solution of PET to a +/− ratio (charge molar ratio) of 8 on the day prior to gene introduction, and after pipetting several times, 4 μl of HA solutions of various concentrations were added and stirred well followed by freezing at −30° C. Subsequently, freeze-drying was carried out to prepare freeze-dried products of the present invention. In addition, a freeze-dried product was prepared using the same method with the exception of changing the mixing order of HA and PEI.
[3] After removing the cultured medium, 500 μl of EMEM containing, 10% FBS, 25 U of penicillin and 25 μg of streptomycin was placed in the wells.
[4] 16 μl of PBS was mixed with the freeze-dried products prepared in [2] followed by incubating for 1 hour and adding to the wells.
[5] The mixtures were incubated for 4 hours at 37° C. in 5% $CO_2$ and 95% air.
[6] The medium was replaced with fresh EMEM containing 10% FBS, 25 U of penicillin and 25 μg of streptomycin followed by incubating for 20 hours at 37° C.
[7] After incubating for 20 hours, the medium was removed followed by the addition of 200 μl of PicaGene cell lysis solution to each well. After allowing to stand for about minutes, the cells were separated from the wells and recovered in microtubes.
[8] Following centrifugation (15,000 rpm, 1 minute), the supernatant was assayed for luciferase. The luciferase assay was carried out according to the procedure provided with the PicaGene Luminescence Kit.

Furthermore, the cell lysis solution was used directly for protein assay. The protein assay was carried out using a protein assay kit (Bio-Rad).

For the sake of comparison, gene expression was investigated for freeze-dried products and non-freeze-dried products to which HA was not added.
[Results]
The results are shown in FIG. 1. In FIG. 1, values in parentheses indicate the ratio of PEI cations and HA anions to plasmid anions, and more specifically, the molar ratio of the charges of PEI and HA to DNA.

In the case of the freeze-dried plasmid/PEI binary complex, expression was 1/1000 or less that prior to freeze-drying, and in contrast to hardly any expression being observed, in the case of addition of HA, high expression was observed, and in the case of freeze-drying after mixing plasmid, PEI and HA at a ratio of 1:8:16 (in terms of charge), expression efficiency with an additional 11% or more higher than the plasmid/PEI binary complex prior to freeze-drying was demonstrated.

Example 2

Effects of Mixing Order

Figure 2:
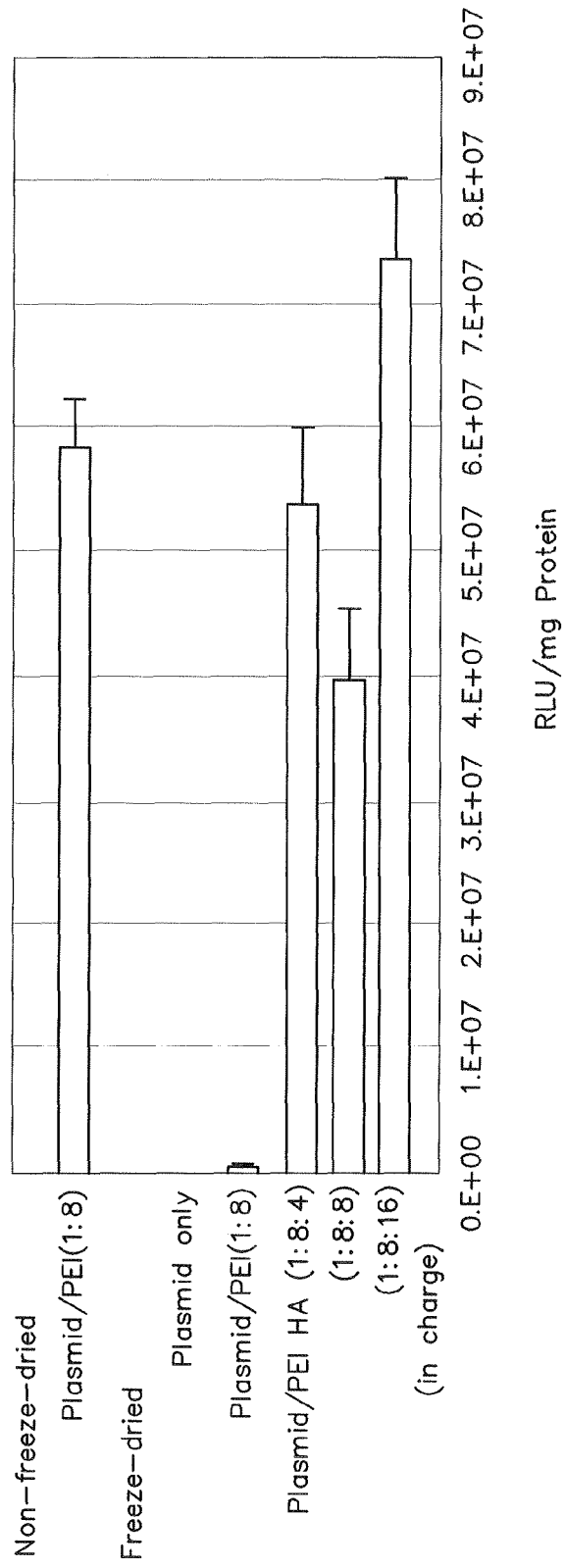
FIG. 2 is a graph showing the results for Example 2.

Freeze-dried products were obtained by mixing with addition of PEI after first adding HA to luciferase plasmid in [2] of Example 1 followed by evaluating in the same manner as Example 1.
[Results]
The results are shown in FIG. 2. In FIG. 2, values in parentheses indicate the ratio of PEI cations and HA anions to plasmid anions and more specifically, indicate the molar ratio of PEI and HA to DNA.

In contrast to hardly any gene expression being observed in the case of the freeze-dried plasmid/PEI binary complex, high expression was observed in the case of addition of HA, and in the case of freeze-drying after mixing plasmid, PEI and HA at a ratio of 1:8:16 (in terms of charge), expression efficiency with an additional 26% or more higher than the plasmid/PEI binary complex prior to freeze-drying was demonstrated. On the basis of these results, high expression was clearly observed even if the order of mixing is changed.

Example 3

Gene Expression by Freeze-Dried Product Containing Plasmid/PEI/PEG Derivation Having Carboxyl Side Chains (PEG-C)

In Example 3, PEG-C having a molecular weight of about 10,000 and containing about 18 carboxyl groups per molecule was used as anionic polymer after synthesizing according to the method described in Non-Patent Document 1 (J. Biomater. Sci. Polymer Edn., Vol. 14, pp. 515-531 (2003)).

A freeze-dried three-component complex comprised of a gene, PEI and PEG-C was incubated with mouse melanoma cell line 316 followed to confirm the expression of luciferase gene.

[Procedure]

[1] B16 cells were seeded into a 24-well multiplate two days prior to gene introduction and then incubated for two nights using EMEM medium.

[2] 12.5 µl of an aqueous solution containing 1.3 µg of luciferase plasmid was mixed with 12.5 µl of an aqueous solution of PEI to a −/− ratio (charge molar ratio) of 8 on the day prior to gene introduction, and after pipetting several times, 25 µl of PEG-C solutions of various concentrations were added and stirred well followed by freezing at −30° C. Subsequently, freeze-drying was carried out to prepare freeze-dried products of the present invention.

[3] After removing the cultured medium, 500 µl of EMEM containing, 10% FBS, 25 U of penicillin and 25 µg of streptomycin was placed in the wells.

[4] 50 µl of PBS was mixed with the freeze-dried products prepared in [2] followed by incubating for 1 hour and adding to the wells.

[5] The mixtures were incubated for 4 hours at 37° C. in 5% $CO_2$ and 95% air.

[6] The medium was replaced with fresh EMEM containing 10% FBS, 25 U of penicillin and 25 µg of streptomycin followed by incubating for 20 hours at 37° C.

[7] After incubating for 20 hours, the medium was removed followed by washing the cells once with PBS and adding 200 µl of PicaGene cell lysis solution to each well. After allowing to stand for about 20 minutes, the cells were separated from the wells and recovered in microtubes.

[8] Following centrifugation (15,000 rpm, 1 minute), the supernatant was assayed for luciferase. The luciferase assay was carried out according to the procedure provided with the PicaGene Luminescence Kit.

Furthermore, the cell lysis solution was used directly for protein assay. The protein assay was carried out using a protein assay kit (Bio-Rad).

In addition, for the sake of comparison, an experiment was carried out in the same manner for a freeze-dried product obtained by adding a neutral polymer PEG, having about the same molecular weight as PEG-C but not having a charge, in an amount equal to that of PEG-C.

[Results]

Figure 3:
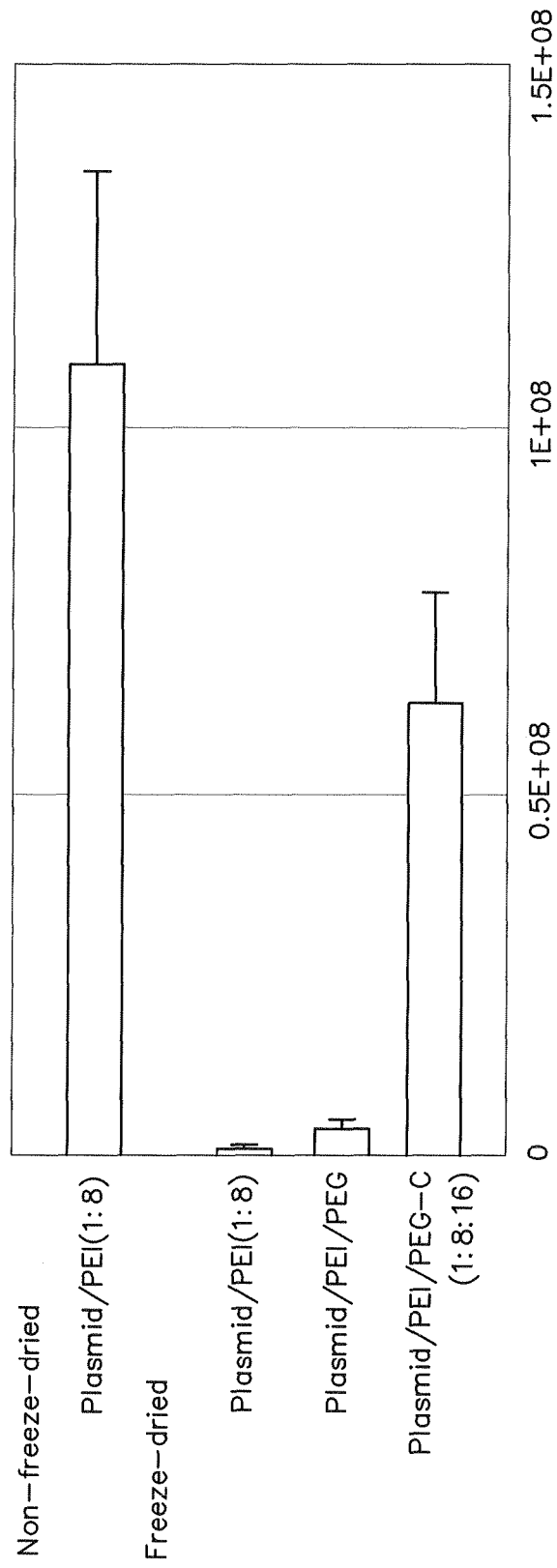
FIG. 3 is a graph showing the results for Example 3.

The results are shown in FIG. 3. In FIG. 3, values in parentheses indicate the ratio of PEI cations and PEG-C anions to plasmid anions, and specifically, the molar ratio of the charges of PEI and PEG-C to DNA.

There was hardly any expression observed in the case of the freeze-dried plasmid/PEI binary complex. In addition, there was hardly any expression observed even following addition of the uncharged PEG. On the other hand, in the case of the freeze-dried product of the present invention to which was added PEG-C, high expression was observed that was nearly 60% of the non-freeze-dried original plasmid/PEI binary complex.

Example 4

Gene Expression by Plasmid/Lipofectamine/HA e-Dried Product

In this example, lipofectamine manufactured by Invitrogen was used for the lipofectamine.

A freeze-dried three-component complex comprised of a gene, lipofectamine and HA was incubated with mouse melanoma cell line derived B16 to confirm the expression of luciferase gene.

[Operation Procedure]

[1] B16 cells were seeded into a 24-well multiplate two days prior to gene introduction and then incubated for two nights using EMEM medium.

[2] 12.5 µl of an aqueous solution containing 1.3 g of luciferase plasmid was mixed with 12.5 µl of an aqueous solution of lipofectamine to a weight ratio of luciferase plasmid to lipofectamine of 8 on the day prior to gene introduction, and after pipetting several times, 25 µl of HA solutions of various concentrations were added and incubated for 30 minutes followed by freezing at −30° C. Subsequently, freeze-drying was carried out to prepare freeze-dried products of the present invention.

[3] After removing the cultured medium, 500 µl of EMEM containing 25 U of penicillin and 25 µg of streptomycin was placed in the wells.

[4] 50 µl of PBS was mixed with the freeze-dried products prepared in [2] followed by incubating for 45 minutes and adding to the wells.

[5] The mixtures were incubated for 4 hours at 37° C. in 5% $CO_2$ and 95% air.

[6] 100 µl of fresh EMEM containing 25 U of penicillin and 25 µg of streptomycin and 400 µl of FBS were added followed by incubating for 20 hours at 37° C.

[7] After incubating for 24 hours, the medium was removed followed by washing the cells once with PBS and adding 200 µl of PicaGene cell lysis solution to each well. After allowing to stand for about 20 minutes, the cells were separated from the wells and recovered in microtubes.

[8] Following centrifugation (15,000 rpm, 1 minute), the supernatant was assayed for luciferase. The luciferase assay was carried out according to the procedure provided with the PicaGene Luminescence Kit.

Furthermore, the cell lysis solution was used directly for protein assay. The protein assay was carried out using a protein assay kit (Bio-Rad)

For the sake of comparison, gene expression was investigated for freeze-dried and non-freeze-dried products to which HA was not added.

In addition, a similar study was carried out by carrying out the incubation of cells and DNA complex of [3] in EMEM medium containing 80% FBS. In this case, instead of adding PBS in [6], 1500 µl of EMEM only containing 25 U of penicillin and 25 µg of streptomycin was added.

[Results]

Figure 4A:
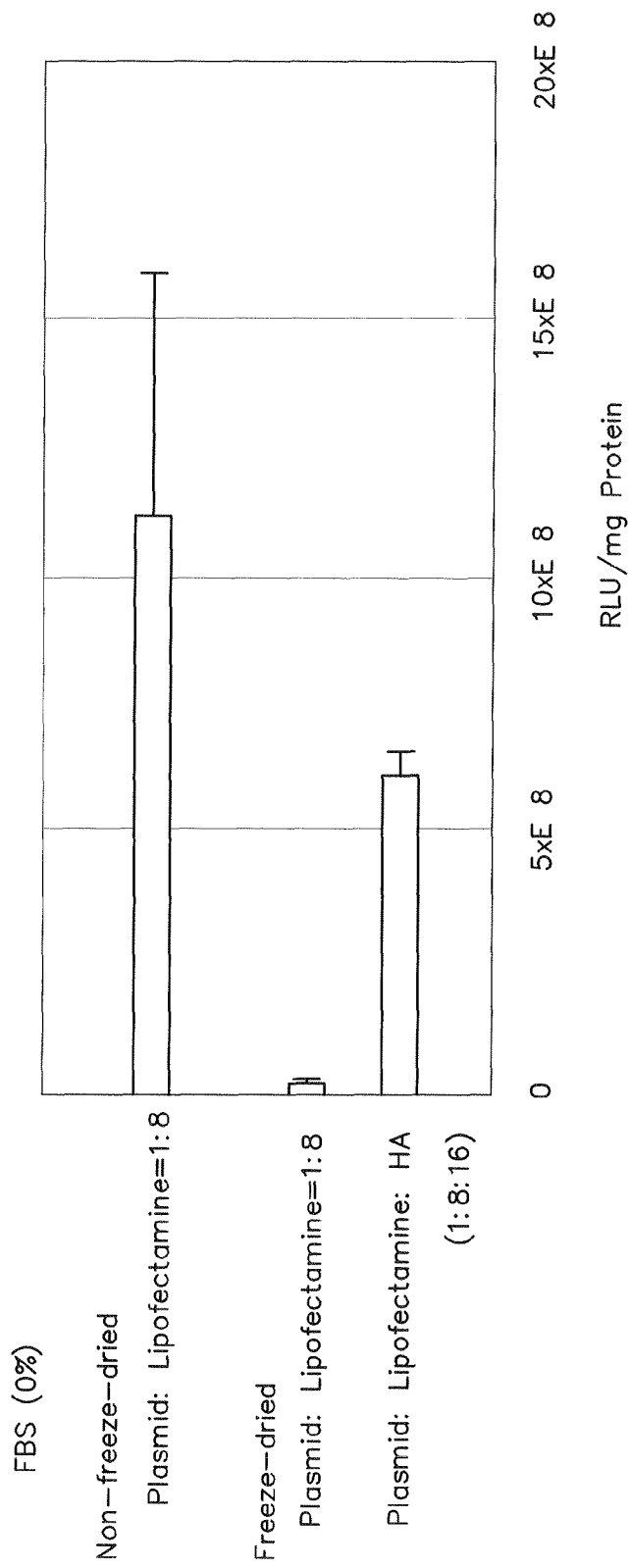
FIGS. 4A and 4B are graphs showing the results for Example 4.
Figure 4B:
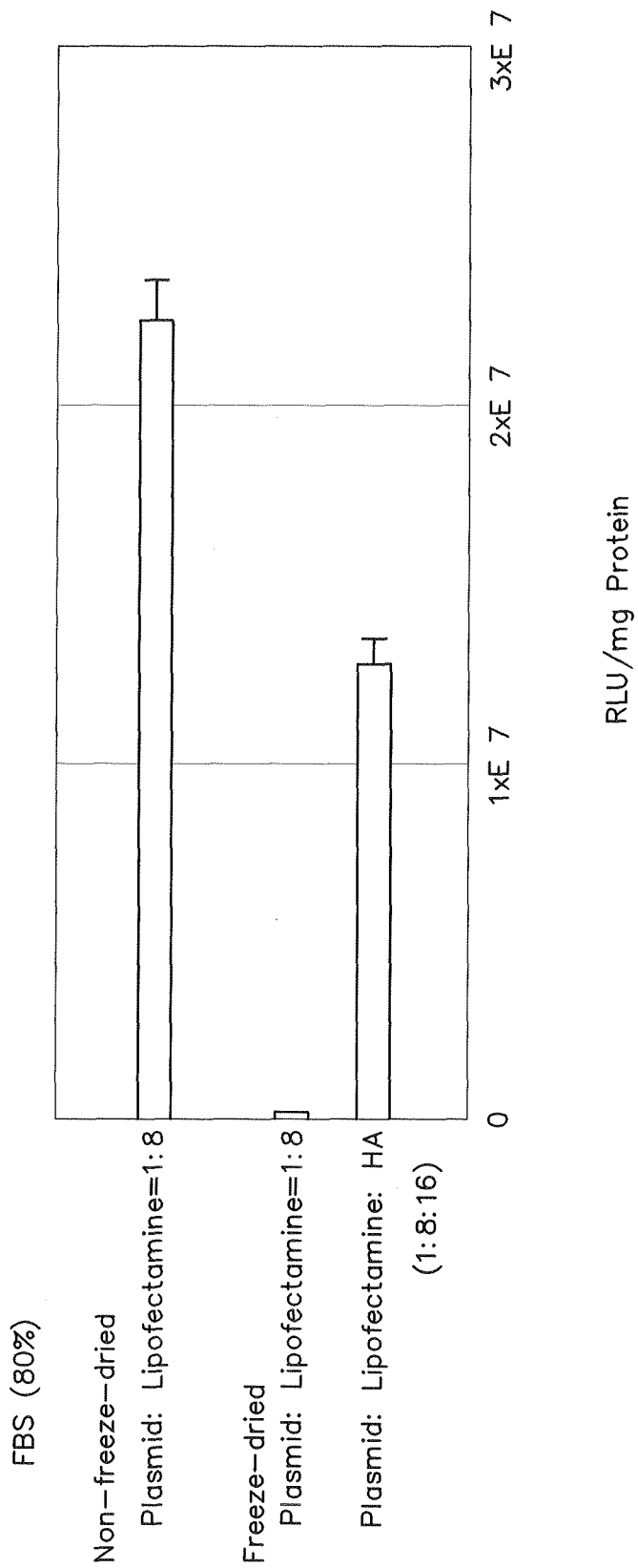

The results are shown in FIGS. 4A and 4B. In FIGS. 4A and 4B, values in parentheses indicate the weight ratio of lipofectamine and HA to plasmid.

In the case of gene introduction in medium not containing FBS, expression in the case of the freeze-dried plasmid/lipofectamine binary complex was 1/3000 or less that prior to freeze-drying, and hardly any expression was observed. In contrast, in the case of addition of HA, expression of about 55% of the non-freeze-dried original plasmid/lipofectamine binary complex was demonstrated.

In the presence of 80% serum, although expression by the freeze-dried plasmid/lipofectamine binary complex decreased further, the freeze-dried plasmid/lipofectamine/HA tertiary complex exhibited high expression of about 57% of the non-freeze-dried original plasmid/lipofectamine binary complex.

Example 5

GENE Expression by Plasmid/Lipofectamine/PEG-C Freeze-Dried Product

The same experiment as Example 4 was carried out using PEG-C having a charge ratio of 16 relative to the plasmid DNA instead of HA. More specifically, instead of adding 25 µl of HA solution as in Example 4, an amount of PEG-C was dissolved in water so that the charge ratio was 16 times that of the plasmid DNA as described in the following graph and added at a final volume of 25 µl.

Gene introduction was carried out in serum-free medium or medium containing 80% serum.

[Results]

The results are shown in FIGS. 5A and 5B. In FIGS. 5A and 5B, values in parentheses indicate the weight ratio of lipofectamine and PEG-C to DNA.

In contrast to hardly any expression being observed in the case of freeze-dried DNA/lipofectamine binary complex, high expression was demonstrated following addition of PEG-C, and in the presence of 80% serum, the plasmid/lipofectamine/PEG-C tertiary complex demonstrated high expression efficiency four times or more the non-freeze-dried original plasmid/lipofectamine binary complex.

Example 6

Effect of Changes in Concentration Before and After Freeze-Drying

A liquid was prepared at a low concentration using 10 times the amount of solvent as in [2] of Example 5 followed by mixing, freeze-drying, adding 50 µl of PBS in the same manner as [4] of Example 5, and similarly evaluating the rehydrated product.

[Results]

Figure 6:
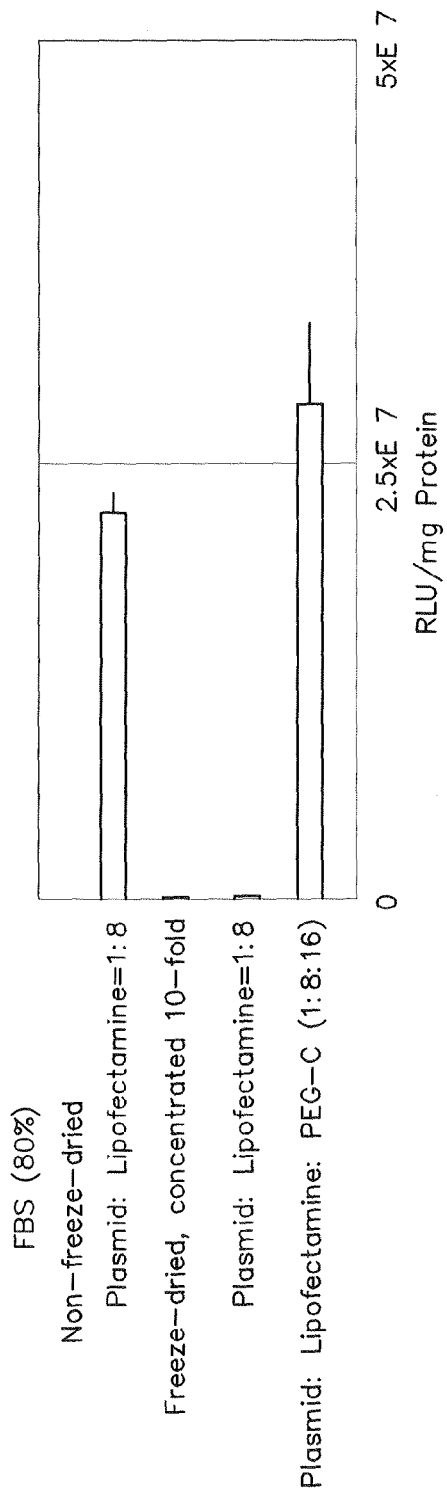
FIG. 6 is a graph showing the results for Example 6.

The results are shown in FIG. 6. In FIG. 6, values in parentheses indicate the weight ratio of lipofectamine and PEG-C to DNA.

In contrast to hardly any expression being observed in the case of freeze-dried DNA/lipofectamine binary complex, with expression of 1/1000 or less that prior to freeze-drying, high expression was observed in the case PEG-C was added, even when concentrated after freeze-drying. In the presence of 80% serum, plasmid/lipofectamine/PEG-C tertiary complex demonstrated high expression efficiency nearly 30% more than the non-freeze-dried original plasmid/lipofectamine binary complex.

On the basis of these results, arbitrary concentrations of complex suspensions or solutions capable of facilitating gene introduction were confirmed to be able to be prepared as a result of freeze-drying.

Example 7

Administration of Freeze-Dried Solid DNA Complex to Living Organism

[Procedure]

50 µl of a TE buffer solution of luciferase-encoded plasmid (0.8 mg/ml) was diluted with 400 µl of water followed by the addition of 100 µl of aqueous hyaluronic acid solution (5.8 mg/ml) and finally the addition of 50 µl of PEI solution (1.25 mg/ml). Thirty minutes after mixing the three components, the mixture was freeze-dried at −30° C. followed by freeze-drying to obtain a solid complex.

$4.72 \times 10^6$ mouse melanoma cell line derived B16 suspended in 100 µl of medium*1 was subcutaneously transplanted into 5-week-old, male ddY mice. When the tumors had reached 6 to 8 mm, an incision was made in the tumor portion under anesthesia and the solid DNA/PEI/HA complex described above was implanted within the tumor followed by suturing the incision.

Two days later, the mice were sacrificed with ether, the tumors and skin were excised and then homogenized in 1 ml of cell lysis solution*2. Subsequently, centrifugation was carried out for 20 minutes at 10,000 rpm and 4° C., and a substrate (Promega, 20 µl) was added to the supernatant (5 µl) to measure the luminescence of the luciferase for seconds with a luminometer.

Total protein was quantified by adding 20 µl of supernatant of each sample diluted 1/80 to 1 ml of protein quantification reagent (Bio-Rad) followed by measuring absorbance at a wavelength of 595 nm 20 minutes later.

[Results]

Figure 7:
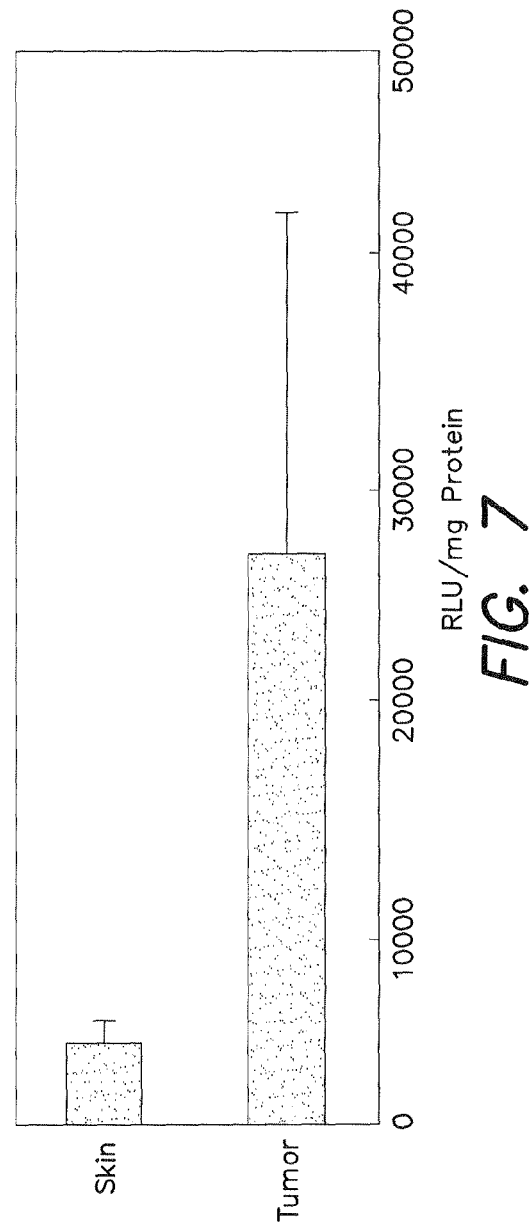
FIG. 7 is a graph showing the results for Example 7.

The solid DNA complex demonstrated extremely high expression within the tumor (results are shown in FIG. 7).

*1 medium; EMEM medium (containing 10% FBS, penicillin G sodium (100 units/ml) and streptomycin sulfate (0.1 mg/ml))

*2 cell lysis solution; 0.05% Triton X-100, 2 mM EDTA and 0.1 M Tris-HCl (pH 7.5)

Example 8

Gene Introduction into Cells on a Culture Plate Using Freeze-Dried DNA Complex

[Procedure]

1.56 µl of a solution of luciferase-encoded plasmid (0.8 mg/ml) was diluted with 12.5 µl of water followed by the addition of 1.56 µl of PEI solution (1.25 mg/ml) and finally the addition of 3.56 µl of aqueous hyaluronic acid solution (5.8 mg/ml). After mixing the three components, the mixture was placed in the wells of a culture plate, frozen at −30° C. 30 minutes later, and subsequently freeze-dried. A mixture to which hyaluronic acid was not added was similarly freeze-dried. In addition, a mixture using a fresh suspension without freeze-drying was simultaneously compared.

$1.2 \times 10^5$ mouse melanoma cell line derived B16 suspended in 300 µl of medium*1 was seeded into the wells containing freeze-dried DNA complex. 1 ml of medium was added 4 hours later and was replaced with 1 ml of fresh medium 20 hours later. 24 hours later, 200 µl of cell lysis solution (Promega) were added and the cells were harvested followed by centrifuging for 1 minute at 15,000 mm and 4° C., adding a substrate (Promega, 20 µl) to the supernatant (5 µl), and measuring the luminescence of the luciferase for 30 seconds with a luminometer.

Total protein was quantified by adding 20 µl of supernatant of each sample diluted 1/5 to 1 ml of protein quantification reagent (Bio-Rad) followed by measuring 5, absorbance at a wavelength of 595 nm 20 minutes later.

*1 medium; EMEM medium (containing 10% FBS, penicillin G sodium (100 units/ml) and streptomycin sulfate (0.1 mg/ml))

[Results]

Figure 8:
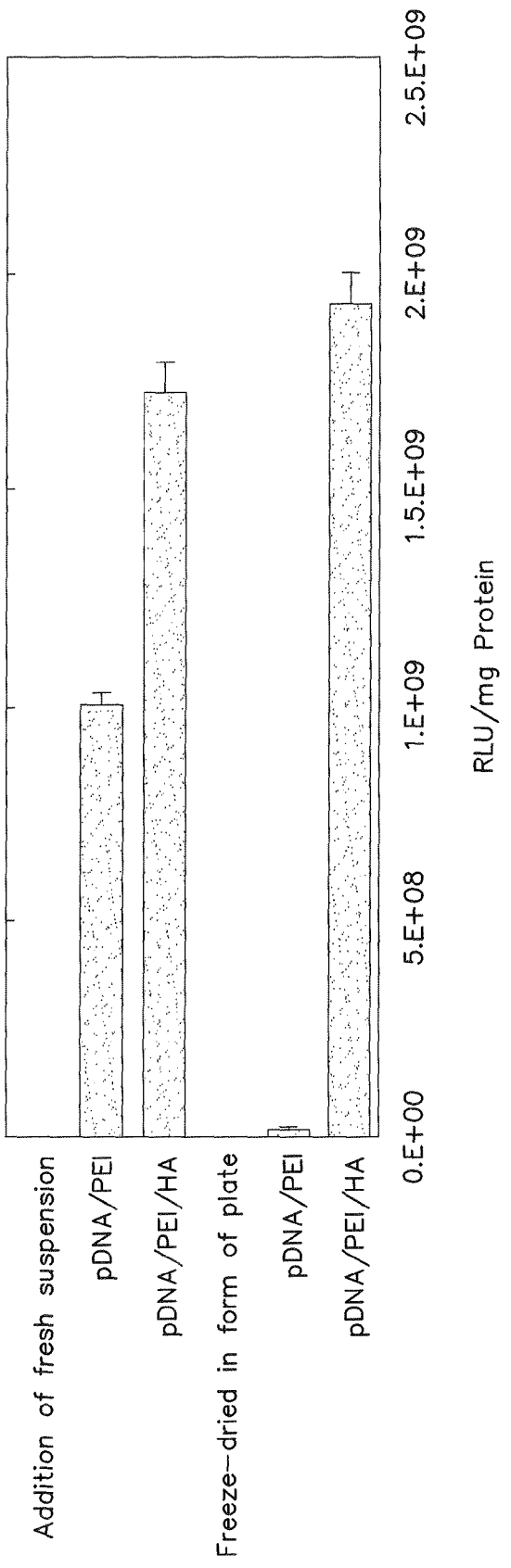
FIG. 8 is a graph showing the results for Example 8.

Although nearly all gene introduction activity had disappeared following freeze-drying in the absence of addition of hyaluronic acid (HA), in the case of addition of HA, high activity similar to that of the fresh suspension was demonstrated even after freeze-drying (results are shown in FIG. 8).

Example 9

In Vivo Gene Introduction Using Suspension of DNA Complex Concentrated by Freeze-Drying

[Operation Procedure]

62.5 μl of a solution of luciferase-encoded plasmid (0.8 mg/ml) was diluted with 0, 500, 2000 or 8000 μl of water followed by the addition of 125 μl of aqueous hyaluronic acid solution (5.8 mg/ml) and finally the addition of 62.5 μl of PET solution (1.25 mg/ml). Thirty minutes after mixing the three components, the mixtures were frozen at −30° C. followed by freeze-drying.

The freeze-dried DNA complexes were resolvated with 250 μl of 5% glucose.

$4.72 \times 10^6$ mouse melanoma cell line derived 316 suspended in 100 μl of medium*1 was subcutaneously transplanted into 5-week-old, male ddY mice. When the tumors had reached 6 to 8 mm, a suspension of resolvated DNA complex was administered into a tail vein of the mice.

The mice were exsanguinated under ether anesthesia 24 hours later followed by excision of the tumor, liver and lungs and homogenizing in 1 ml of cell lysis solution*2. Subsequently, centrifugation was carried out for 20 minutes at 10,000 rpm and 4° C., and a substrate (Promega, 20 μl) was added to the supernatant (5 μl) to measure the luminescence of the luciferase for 30 seconds with a luminometer.

Total protein was quantified by adding 20 μl of supernatant of each sample diluted 1/80 to 1 ml of protein quantification reagent (Bio-Rad) followed by measuring absorbance at a wavelength of 595 nm 20 minutes later.

*1 medium; EMEM medium (containing 10% FBS, penicillin G sodium (100 units/ml) and streptomycin sulfate (0.1 mg/ml))

*2 cell lysis solution; (0.05% Triton X-100, 2 mM EDTA and 0.1 M Tris-HCl (pH 7.5))

[Results]

Figure 9:
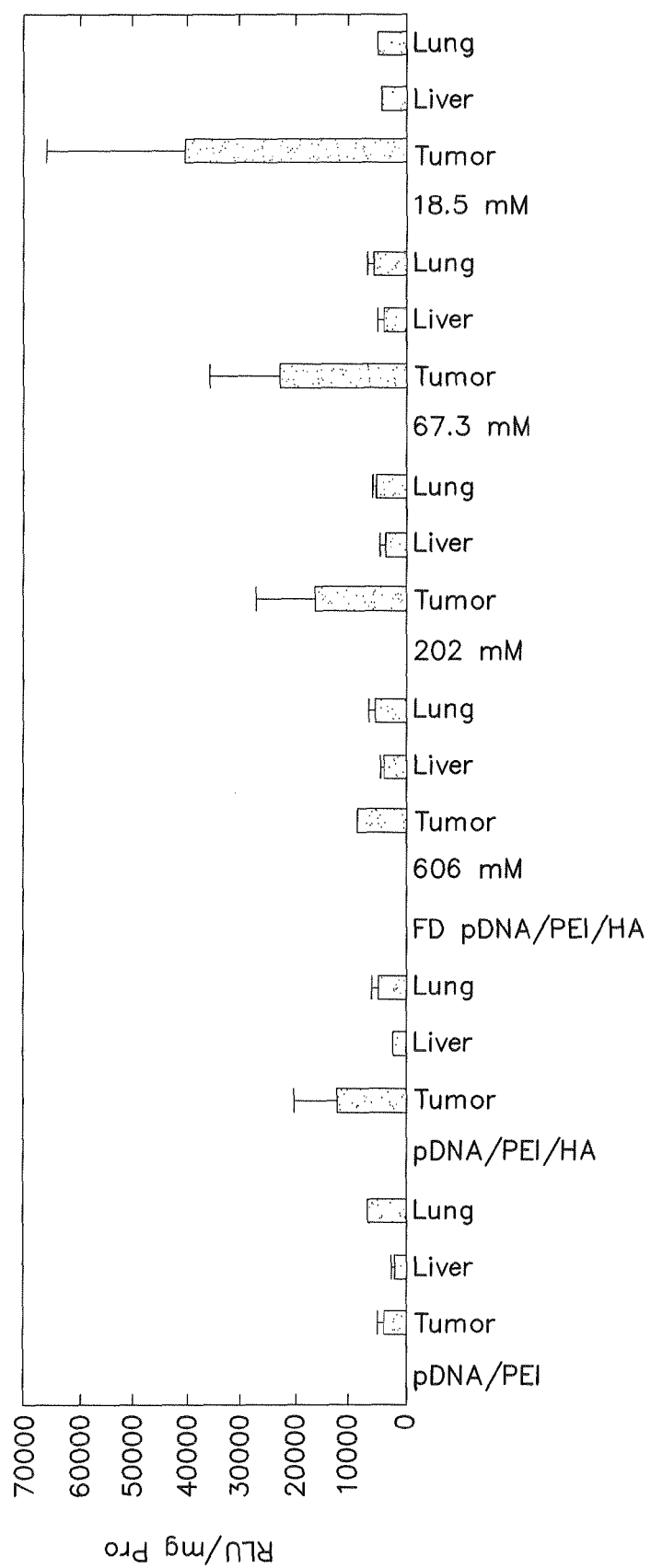
FIG. 9 is a graph showing the results for Example 9.

The results are shown in FIG. 9. Concentrations in the graph indicate the final concentrations of DNA at the time of complex preparation as the nucleic acid base concentrations. In the case of freeze-drying following addition of hyaluronic acid (HA), higher gene expression was observed the lower the concentration of DNA at the time of preparation, and remarkably high luciferase activity was demonstrated within the tumor in particular.

Example 10

Gene Expression Inhibitory Effects by siRNA Complex Freeze-Dried on a Culture Plate

[Operation Procedure]

25 μl of a protamine aqueous solution (78 μg/ml) was added to 25 μl of an aqueous solution of anti-luciferase siRNA (Invitrogen, 21.28 μg/ml) followed by the addition of 50 μl of hyaluronic acid solution (53.7 μg/ml or 107.5 μg/ml). After mixing the three components, the mixtures were placed in the wells of a culture plate, frozen at −30° C. for 30 minutes and subsequently freeze-dried.

$1.2 \times 10^5$ mouse melanoma cell line derived B16 suspended in 100 μl of medium*1 was seeded onto a culture plate followed by the addition of 1 ml of medium 4 hours later and the addition of a mixture of 25 μl of pDNA solution (50 μg/ml) and 25 μl of PEI solution (78 μg/ml). Moreover, the medium was replaced with 1 ml of fresh medium 20 hours later.

24 hours later, 200 μl of cell lysis solution (Promega) was added and the cells were harvested followed, by centrifuging for 1 minute at 15,000 rpm and 4° C., adding substrate (Promega, 20l) to the supernatant (5 μl), and measuring the luminescence of the luciferase for 30 seconds with a luminometer.

Total protein was quantified by adding 20 μl of supernatant of each sample diluted 1/5 to 1 ml of protein quantification reagent (Bio-Rad) followed by measuring absorbance at a wavelength of 595 nm 20 minutes later.

*1 medium; EMEM medium (containing 10% FBS, penicillin G sodium (100 units/ml) and streptomycin sulfate (0.1 mg/ml)).

Mixtures to which protamine and hyaluronic acid were not added were also similarly freeze-dried.

[Results]

Figure 10:
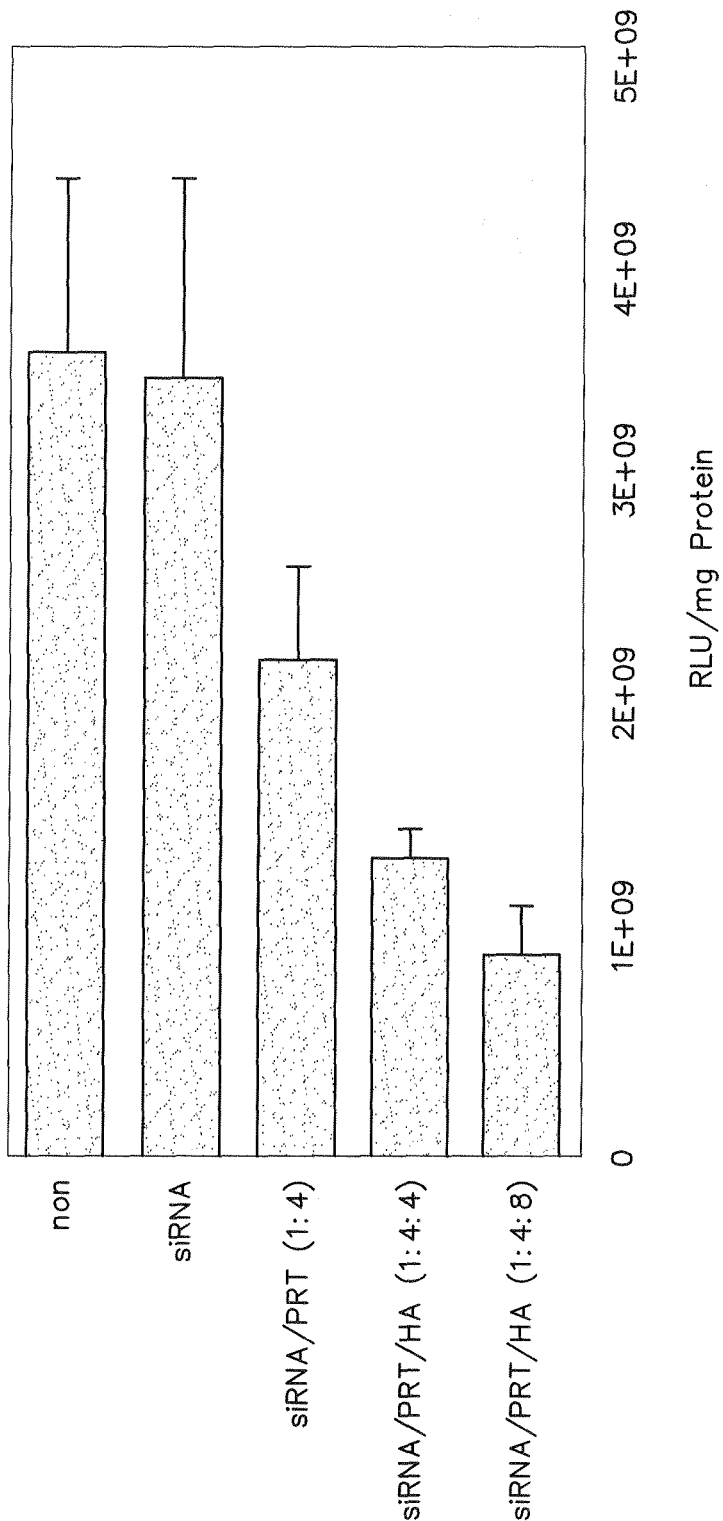
FIG. 10 is a graph showing the results for Example 10.

Expression of luciferase was significantly inhibited in cells cultured on plate which had been freeze-dried following the addition of protamine (PRT) and hyaluronic acid (HA) (refer to FIG. 10).

Example 11

Size of DNA Complexes Prepared at Different Concentrations Following Rehydration

[Operation Procedure]

1.5 μl of the same solution of luciferase plasmid as used in Example 1 (0.8 mg/ml) was diluted with 0, 12.5 or 200 μl of water followed by the addition of 3 μl of aqueous hyaluronic acid solution (5.8 mg/ml) and finally the addition of 1.5 μl of PET solution (1.25 mg/ml). Thirty minutes after mixing the three components, the mixtures were frozen at −30° C. followed by freeze-drying.

The freeze-dried DNA complexes were rehydrated with 6 μl of water followed by the addition of 800 μl of water 30 minutes later and measuring the size of the complexes with a zeta analyzer (Malvern Instruments).

[Results]

Figure 11:
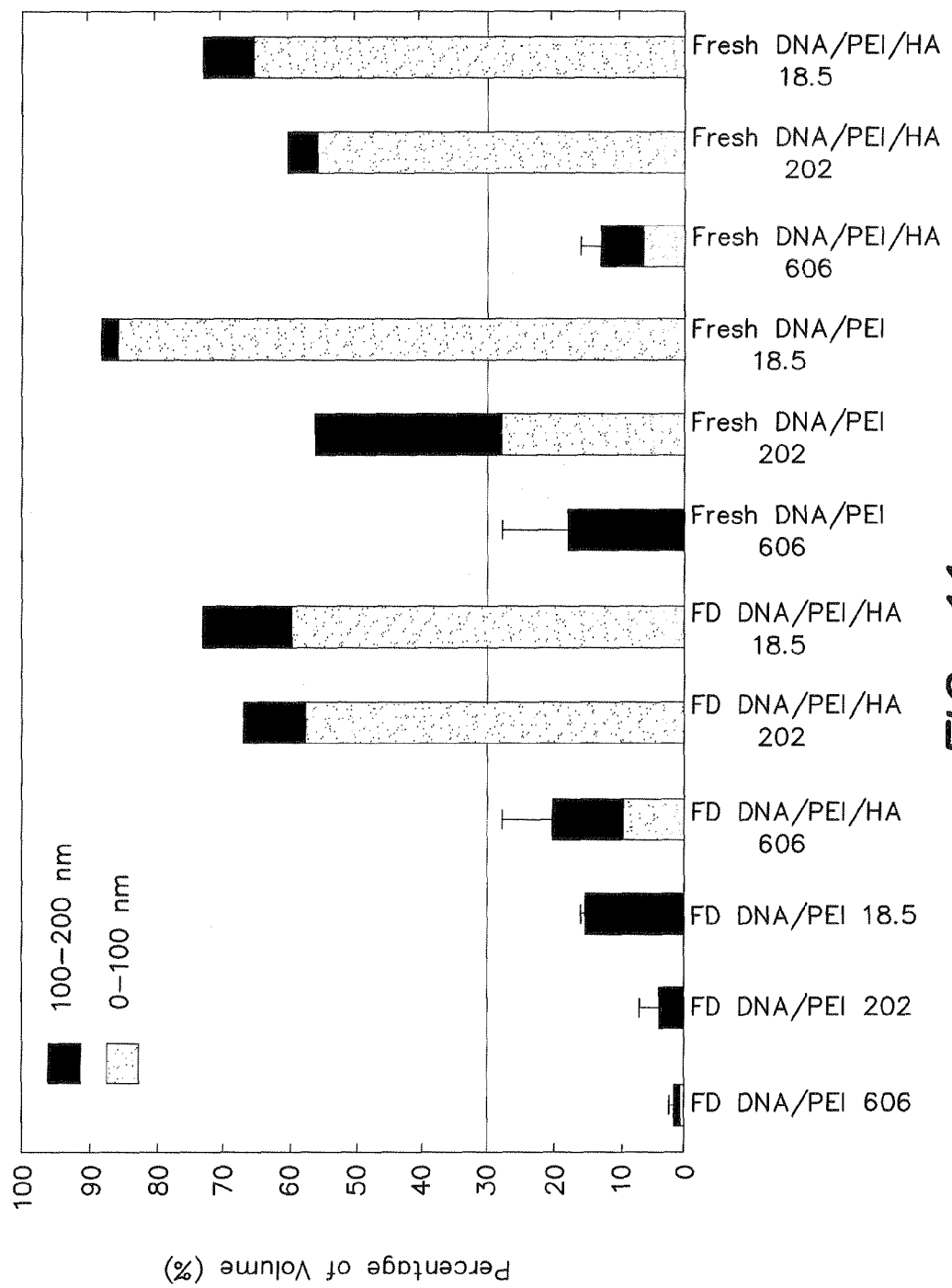
FIG. 11 is a graph showing the results for Example 11.

The percentages of formed complex particles measuring 0 to 100 nm and the percentages of formed complex particles measuring 100 to 200 nm are shown in FIG. 11. The values shown after the names of the components indicate the final DNA concentration at the time of complex preparation as nucleic acid base concentrations.

There were hardly any fine particles observed after rehydration in the case of not adding hyaluronic acid (HA) On the other hand, in the case of freeze-drying following the addition of hyaluronic acid, numerous particles were observed to maintain their small size even after rehydration. In addition, although DNA concentrations following rehydration were the same in all cases, the percentage of fine particles was observed to be greater in the case where the complexes were prepared under the more dilute conditions.

The invention claimed is:

1. A freeze-dried product of a complex containing (i) a nucleic acid or an oligonucleic acid, (ii) polyethyleneimine and (iii) hyaluronic acid or chondroitin sulfate.

2. The freeze-dried product according to claim 1, wherein (iii) is hyaluronic acid.

3. The freeze-dried product according to claim 1, wherein (iii) is chondroitin sulfate.

4. The freeze-dried product according to claim 1, wherein a molar ratio of negative charge positive charge ratio of each charged group of the nucleic acid or the oligonucleic acid to the polyethyleneimine is 1:1 to 1:50; and a molar ratio of negative charge: negative charge ratio of each charged group of the nucleic acid or the oligonucleic acid to the hyaluronic acid or the chondroitin sulfate is 1:1 to 1:60.

* * * * *